US011464716B1

(12) United States Patent
Mustafa

(10) Patent No.: US 11,464,716 B1
(45) Date of Patent: Oct. 11, 2022

(54) SEMI-PERMANENT COLORANT COMPOSITION FOR HAIR

(71) Applicant: AMERICAN SPRAYTECH, L.L.C., North Branch, NJ (US)

(72) Inventor: Aaysha Mustafa, North Brunswick, NJ (US)

(73) Assignee: AMERICAN SPRAYTECH, L.L.C., North Branch, NJ (US)

( * ) Notice: Subject to any disclaimer, the term of this patent is extended or adjusted under 35 U.S.C. 154(b) by 30 days.

(21) Appl. No.: 16/111,332

(22) Filed: Aug. 24, 2018

Related U.S. Application Data

(60) Provisional application No. 62/552,621, filed on Aug. 31, 2017.

(51) Int. Cl.

| | |
|---|---|
| *A61K 9/12* | (2006.01) |
| *A61Q 5/12* | (2006.01) |
| *A61Q 5/00* | (2006.01) |
| *A61Q 5/06* | (2006.01) |
| *A61Q 5/10* | (2006.01) |
| *A61K 8/04* | (2006.01) |
| *A61K 8/81* | (2006.01) |
| *A61K 8/42* | (2006.01) |
| *A61K 8/34* | (2006.01) |
| *A61K 8/49* | (2006.01) |
| *A61K 8/46* | (2006.01) |
| *A61K 8/73* | (2006.01) |
| *A61K 8/31* | (2006.01) |
| *A61K 8/41* | (2006.01) |

(52) U.S. Cl.
CPC .............. *A61K 8/046* (2013.01); *A61K 8/315* (2013.01); *A61K 8/342* (2013.01); *A61K 8/416* (2013.01); *A61K 8/42* (2013.01); *A61K 8/463* (2013.01); *A61K 8/4973* (2013.01); *A61K 8/731* (2013.01); *A61K 8/732* (2013.01); *A61K 8/8111* (2013.01); *A61Q 5/065* (2013.01); *A61K 2800/432* (2013.01); *A61K 2800/524* (2013.01); *A61K 2800/596* (2013.01)

(58) Field of Classification Search
CPC ... A61Q 5/12; A61Q 5/06; A61Q 5/00; A61Q 5/04; A61Q 5/065; A61Q 5/10; A61K 2800/00; A61K 2800/594; A61K 2800/5424; A61K 2800/48; A61K 2800/10; A61K 8/8152; A61K 2800/5426; A61K 8/046; A61K 8/732; A61K 2800/432
See application file for complete search history.

(56) References Cited

U.S. PATENT DOCUMENTS

| | | | |
|---|---|---|---|
| 4,000,077 A | 12/1976 | Wixon | |
| 4,786,422 A | 11/1988 | Kern | |
| 4,873,079 A | 10/1989 | Hahn et al. | |
| 4,888,119 A | 12/1989 | Klewsaat | |
| 4,929,367 A | 5/1990 | Thomas et al. | |
| 5,415,857 A | 5/1995 | Robbins et al. | |
| 5,679,114 A | 10/1997 | Haning et al. | |
| 6,042,619 A | 3/2000 | Haning et al. | |
| 6,106,578 A * | 8/2000 | Jones | A61K 8/87 8/405 |
| 6,413,505 B1 * | 7/2002 | Vitale | A61Q 5/06 424/70.11 |
| 2001/0003851 A1 * | 6/2001 | Hickling | A61K 8/345 8/428 |
| 2006/0263314 A1 * | 11/2006 | Ivanova | A61K 8/046 424/70.7 |
| 2008/0189876 A1 | 8/2008 | Trigg et al. | |
| 2009/0300858 A1 | 12/2009 | Bong-Lim et al. | |
| 2010/0313362 A1 * | 12/2010 | Vainshelboim | A61K 8/97 8/425 |
| 2011/0250148 A1 | 10/2011 | Mateu et al. | |
| 2011/0250249 A1 | 10/2011 | Mateu et al. | |
| 2013/0164242 A1 * | 6/2013 | Tamareselvy | A61K 8/8152 424/70.7 |
| 2013/0206096 A1 * | 8/2013 | Hampton | F16J 9/20 123/193.6 |
| 2013/0306096 A1 * | 11/2013 | Savaides | A61Q 5/12 132/206 |
| 2014/0094558 A1 | 4/2014 | Mateu et al. | |
| 2014/0336308 A1 | 11/2014 | Mateu et al. | |
| 2015/0164752 A1 * | 6/2015 | Vena | A61K 8/046 8/406 |
| 2015/0335129 A1 | 11/2015 | Sorrels | |
| 2016/0008264 A1 | 1/2016 | Greene | |

FOREIGN PATENT DOCUMENTS

| | | | | |
|---|---|---|---|---|
| EP | 1779893 A1 * | 5/2007 | ............ | A61K 8/37 |
| WO | WO-2012059411 A1 * | 5/2012 | ............ | A61K 8/046 |
| WO | 2016159522 A1 | 10/2016 | | |

* cited by examiner

*Primary Examiner* — Tracy Liu

(74) *Attorney, Agent, or Firm* — Renner, Kenner, Greive, Bobak, Taylor & Weber

(57) ABSTRACT

A semi-permanent colorant composition is provided that is exhibits excellent color deposit without heat or oxidative treatment, and resists fading throughout several washes.

17 Claims, No Drawings

SEMI-PERMANENT COLORANT COMPOSITION FOR HAIR

FIELD OF THE INVENTION

One or more embodiments of the present invention relate to semi-permanent colorant compositions for hair and dispensers and method of use thereof.

BACKGROUND OF THE INVENTION

A hair dyeing composition may be classified into three groups: temporary hair coloring, semi-permanent hair coloring, and permanent hair coloring. The classification is made primarily based upon the persistence of color in the hair.

Typically, there are two steps in a permanent color treatment: opening up the hair shaft and adding color. In contrast, semi-permanent color treatment simply adds color. Some typical features of semi-permanent hair color treatment are: also called hair gloss; adds shine; available in clear if a color change is not desired; may be used to refresh or change tone; does not lighten or darken hair; no developer-activator required; no mixing required; the color product is applied directly on hair; user may apply as much or as little as needed for the amount of color desired; color lasts up to about eight shampoos; does not change hair structure or color permanently; not designed for gray coverage.

United States Patent Application Pub. No. 2009/0300858 A1 discloses a semi-permanent hair dyeing composition, and teaches that if acrylate copolymer is used as a hydrophobic polymer for forming a waterproof coating in the acid semi-permanent hair dyeing composition, and simultaneously, N-methyl pyrrolidone is used as an organic solvent for acrylate copolymer, the dye fastened to the hair surface is surrounded with a hydrophobic waterproof coating, which results in preventing the dye from being dissolved by rainwater or sweat.

United States Patent Application Pub. No. 2015/0335129 A1 describes the need for a temporary hair coloring system and method that may be used without the assistance of a hair color professional, and thus, without the expense, inconvenience, and time-consuming nature associated with traveling to a salon and hiring a hair color professional. The patent application discloses a system and method of applying temporary hair color dye, using temporary powder dyes ("powder dyes") of various colors, to the roots of hair. This system provides only a temporary hair color.

Thus, there continues to exist a need for hair color compositions and methods that are semi-permanent and that do not require large amounts of organic solvent.

SUMMARY OF THE INVENTION

The present invention provides methods and compositions relating to a water-based aerosol mousse semi-permanent colorant composition for hair and dispensers and method of use thereof. One or more embodiments provides a semi-permanent colorant mousse concentrate that includes at least one foam boosting surfactant, at least one cold process formulation agent, at least one colorant, optionally, one or more viscosity modifiers, optionally, one or more hair conditioning agents, optionally, one or more preservatives, and at least a minimum amount of an aqueous solvent. The mousse concentrate may be aerosolized with a propellant to form a water-based aerosol mousse semi-permanent colorant composition.

Other embodiments provide a method for coloring hair semi-permanently. The method includes the steps of providing an aerosolized mousse semi-permanent colorant composition according to the present invention, massaging an amount of the colorant composition onto hair, allowing the composition to remain on the hair for an effective period of time, and rinsing the excess composition from the hair. Advantageously, heat is not required, and the color will remain throughout at least ten washes.

DETAILED DESCRIPTION OF ILLUSTRATIVE EMBODIMENTS

In one or more embodiments, a water-based semi-permanent colorant composition is provided that may be aerosolized to form a mousse. The water-based composition includes a foam boosting surfactant, at least one cold process formulation agent, at least one colorant, optionally, one or more viscosity modifiers, optionally, one or more hair conditioning agents, optionally, one or more preservatives, and at least a minimum amount of an aqueous solvent.

The semi-permanent colorant composition may thus be described in terms of two portions: the propellant, and all other ingredients. All ingredients other than the propellant may be referred to as a semi-permanent colorant mousse concentrate. Accordingly, when discussing the effective amounts of components within the semi-permanent colorant composition, the amounts may be stated based upon the mousse concentrate, and may also be stated based upon the total semi-permanent colorant composition, i.e. including the propellant.

In one or more embodiments, the semi-permanent colorant composition includes a propellant. Propellants can be used individually or blended together. Advantageously, the selection of a propellant or blend of propellants may be used to achieve a particular spray pattern, control particle size, conform to government regulations, or for cost considerations.

Propellants may be selected from the group consisting of hydrocarbons, hydrofluorocarbons, ethers, and combinations thereof. Examples of hydrocarbon propellants include pentane, n-butane, isobutane, and propane. Examples of hydrofluorocarbon propellants include 1,1,1,2-tetrafluoroethane (134a) and 1,1-difluoroethane (152a). An example of an ether propellant includes dimethyl ether. In one or more embodiments, the propellant includes butane and propane.

In one or more embodiments, the propellant includes from about 20 to about 40 wt. % propane, and in other embodiments, from about 30 to about 35 wt. % propane, based upon the total weight of propellant. In these or other embodiments, the propellant includes from about 50 to about 80 wt. % propane, in other embodiments, from about 60 to about 75 wt. % propane, based upon the total weight of propellant.

In one or more embodiments the total amount of propellant is from about 2 to about 97 wt. %, in other embodiments from about 4 to about 90 wt. %, and in other embodiments from about 5 to about 80 wt. %, based upon the total weight of the semi-permanent colorant composition. In one or more embodiments the total amount of propellant is from about 2 to about 20 wt. %, in other embodiments from about 4 to about 15 wt. %, and in other embodiments from about 5 to about 10 wt. %, based upon the total weight of the semi-permanent colorant composition.

"Mousse," for purposes herein, refers to an aerosolized, creamy foam. Mousse concentrate refers to a liquid composition that is capable of forming a mousse upon being dispensed from an aerosol dispenser. In one or more embodiments, the semi-permanent colorant mousse concentrate includes at least one foam boosting surfactant, at least one cold process formulation agent, at least one colorant, optionally, one or more viscosity modifiers, optionally, one or more hair conditioning agents, optionally, one or more preservatives, and at least a minimum amount of an aqueous solvent.

The foam boosting surfactant may be selected from anionic, nonionic, amphoteric, and zwitterionic surfactants. In one or more embodiments, the foam boosting surfactant is sulfate-free. Advantageously, sulfate-containing surfactants can be omitted.

In one or more embodiments, the foam boosting surfactant is a nonionic surfactant. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, and alkylpolyglycosides. Specific examples of suitable nonionic surfactants include alkanolamides such as cocamide DEA, cocamide MEA, cocamide MIPA, lauramide DEA, and lauramide MEA, alkyl amine oxides such as lauramine oxide, cocamine oxide, cocamidopropylamine oxide, and lauramidopropylamine oxide, sorbitan laurate, sorbitan distearate, fatty acids or fatty acid esters such as lauric acid, and isostearic acid, fatty alcohols or ethoxylated fatty alcohols such as lauryl alcohol, laureth-4, laureth-7, laureth-9, laureth-40, trideceth alcohol, 011-15 pareth-9, C12-13 Pareth-3, and C14-15 Pareth-11, alkylpolyglucosides such as decyl glucoside, lauryl glucoside, and coco glucoside.

In one or more embodiments, the foam boosting surfactant is a zwitterionic surfactant. Examples of suitable zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

In one or more embodiments, the foam boosting surfactant is an amphoteric surfactant. Examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one or more embodiments, the foam boosting surfactant is an anionic surfactant. Examples of sulfate free anionic surfactants include monoalkyl phosphates, dialkyl phosphates, sarcosinates, sulfosuccinates, isethionates, and taurates and mixtures thereof, mild anionic amino acid based surfactants such as sodium cocoyl glycinate, sodium lauryl glycinate, sodium cocoyl alinate, glutamates, and mixtures thereof. Specific examples include lauramidopropyl hydroxysultaine, sodium lauroamphoacetate, sodium cocoyl glycinate, sodium methyl cocoyl taurate, and decyl glucoside, sodium-monoalkyl phosphates, sodium dialkyl phosphates, sodium lauroyl sarcosinate, lauroyl sarcosine, cocoyl sarcosinate, sodium cocoyl isethionate, disodium laureth sulfosuccinate, sodium methyl oleoyl taurate, sodium methyl cocoyl taurate, sodium laureth carboxylate, sodium trideceth carboxylate.

Foam boosting surfactants are further described in U.S. Patent App. Pub. Nos. 2017/0071836 A1, 2011/0139170 A1, and 2015/0335555 A1, International (PCT) Patent App. Pub. No. WO 2010/020516 A1, and U.S. Pat. No. 9,480,629, all of which are incorporated herein by reference.

In one or more embodiments, the amount of foam boosting surfactant is from about 0.1 wt. % to about 75 wt. %, in other embodiments, from about 0.5 wt. % to about 50 wt. %, in other embodiments, from about 1 wt. % to about 20 wt. %, and in other embodiments, from about 2 wt. % to about 10 wt. %, based upon the total weight of the mousse concentrate.

In one or more embodiments, the amount of foam boosting surfactant is from about 0.1 wt. % to about 75 wt. %, in other embodiments, from about 0.5 wt. % to about 50 wt. %, in other embodiments, from about 1 wt. % to about 20 wt. %, and in other embodiments, from about 2 wt. % to about 10 wt. %, based upon the total weight of the aerosol semi-permanent colorant composition, including propellant.

In one or more embodiments, the mousse concentrate comprises at least one cold process formulation agent (CPFA). A cold process formulation agent may eliminate or reduce the need for traditional emulsifiers and allow the addition of waxy component into the composition without heating. In one or more embodiments, the CPFA forms a stable emulsion when introduced into aqueous solutions at room temperature.

Typically, CPFAs include a waxy component and a polymer having a backbone, and pendant groups thereon that are pendant ionic or ionizable groups. In one or more embodiments, the CPFA includes ceteraryl alcohol, behentrimonium chloride, and polyquaternium-37.

CPFAs are commercially available, for example under the tradename Jeesperse ICE, from Jeen International Corporation.

CPFAs are further described in U.S. Patent App. Pub. Nos. 2014/0094558A1, 2011/0250249A1, 2014/0336308A1, and 2011/0250148A1 all of which are incorporated herein by reference.

The amount of the CPFA is not particularly limited, so long as it is understood that the CPFA may increase the viscosity of the composition at higher concentrations. In one or more embodiments, the CPFA may be present in an amount up to about 10 wt. %, in other embodiments, up to about 8 wt. %, and in other embodiments, up to about 5 wt. %, based upon the total weight of the mousse concentrate.

In one or more embodiments, the CPFA may be present in an amount up to about 10 wt. %, in other embodiments, up to about 8 wt. %, and in other embodiments, up to about 5 wt. %, based upon the total weight of the aerosol semi-permanent colorant composition, including propellant.

In one or more embodiments, the mousse concentrate includes at least one semi-permanent colorant. For purposes of this specification, the term colorant is synonymous with the term coloring agent. The colorant may be considered the active ingredient or functional ingredient in the compositions of the present invention. Examples include direct dyes, disperse dyes, acid dyes, and basic dyes.

Basic Dyes—Examples of basic dyes include blues, browns, greens, oranges, reds, and yellows. Suitable blues include Basic Blue 3, 6, 7, 9, 26, 41, 47, and 99. Suitable browns include Basic Browns 4, 16, and 17. Suitable greens include Basic Green 1 and 4. Suitable oranges include Basic Orange 1 and 2. Suitable Reds include Basic Red 1, 2, 22, 46, 76, and 118. Suitable violets include Basic Violet 1, 3, 4, 10, 11:1, 14, and 16. Suitable yellows include Basic Yellow 11, 28, and 57.

HC Dyes—Examples of HC dyes include blue, brown, green, orange, red, violet, and yellow. Suitable blues include HC Blue 2, 4, 5, 6, 7, 8, 9, 10, 11, 12, 13, and 14. Suitable browns include HC Brown 1 and 2. Suitable greens include HC Green 1. Suitable oranges include HC Orange 1, 2, 3, and 5. Suitable reds include HC Red 1, 3, 7, 8, 9, 10, 11, 13, and 14. Suitable violets include HC Violet 1 and 2. Suitable yellows include HC Yellow 2, 4, 5, 6, 7, 8, 9, 10, 11, 13, 14, and 15.

Acid Dyes—Examples of acid dyes include black, blue, brown, green, orange, red, violet, and yellow. Examples of Acid Black are numbers 1 and 52. Suitable blues include Acid Blue 1, 3, 9, 62, and 74, including Lakes thereof. Examples of browns and greens include Acid Brown 13 and Acid Green 1, 25, and 50, respectively. Suitable oranges include Acid Orange 3, 6, 7, and 24. Suitable reds include Acid Red 14, 18, 27, 33, 35, 51, 52, 73, 87, 92, 95, 184, and 195. Suitable violets include Acid Violet 9 and 43. Suitable yellows include Acid Yellow 1, 3, 23, and 73.

Direct and Disperse Dyes—Examples of direct dyes include Direct Black 51, Direct Blue 86, Direct Red 23, 80, and 81; Direct Violet 48, and Direct Yellow 12. Suitable disperse dyes include Disperse Black 9, Disperse Blue 1, 3, and 7; Disperse Brown 1, Disperse Orange 3, Disperse Red 11, 15, and 17; and Disperse Violet 1, 4, and 15.

Dyes are set forth in the International Cosmetic Ingredient Dictionary and Handbook, Personal Care Products Council (PCPC), Sixteenth Edition, 2016, which is incorporated by reference herein.

Colorants can be used individually or as mixtures to achieve the desired colors.

The total amount of the colorant may be stated based upon the mousse concentrate, and may also be stated based upon the total aerosol semi-permanent colorant composition, i.e. including the propellant. The total amount of colorant is not necessarily limited, but may be selected based upon the solubility of the colorant, any applicable safety regulations, the amount of color intensity that is desired, and other factors. In one or more embodiments, including embodiments where acid dyes are employed, the amount colorant may affect the foam structure of the aerosol mousse. In one or more embodiment, the colorant may be employed in amounts up to about 10 wt. %, in other embodiments, up to about 8 wt. %, in other embodiments, up to about 5 wt. %, in other embodiments, up to about 2 wt. %, in other embodiments, up to about 1 wt. %, in other embodiments, up to about 0.5 wt. %, based upon the total weight of the mousse concentrate.

In one or more embodiment, the colorant may be employed in amounts up to about 10 wt. %, in other embodiments, up to about 8 wt. %, in other embodiments, up to about 5 wt. %, in other embodiments, up to about 2 wt. %, in other embodiments, up to about 1 wt. %, in other embodiments, up to about 0.5 wt. %, based upon the total weight of the aerosol semi-permanent colorant composition, including propellant.

In one or more embodiments the amount of colorant is from about 0.001 wt. % to about 20 wt. %, in other embodiments, from about 0.01 wt. % to about 15 wt. %, in other embodiments, from about 0.05 wt. % to about 10 wt. %, based upon the total weight of the mousse concentrate.

In one or more embodiment the amount of colorant is from about 0.001 to about 15 wt. %, in other embodiments from about 0.005 to about 10 wt. %, in other embodiments, from about 0.01 to about 8 wt. %, based upon the total weight of the aerosol semi-permanent colorant composition, including propellant.

The mousse concentrate of the present invention may contain one or more viscosity modifiers. Examples of viscosity modifiers include hydroxyethyl cellulose, methyl cellulose, polyethylene glycol, ethylene glycol, propylene glycol, isoprene glycol, ethanol, starch, modified starch, such as hydroxypropyl starch phosphate, clay minerals, xanthan gum, and salts (such as sodium chloride, ammonium chloride, and sodium citrate). In one or more embodiments, the mousse concentrate includes hydroxypropyl starch phosphate. In one or more embodiments, the viscosity modifier does not include any stearate-based compounds.

Advantageously, the viscosity modifier may be selected to achieve a mousse concentrate that is pourable at room temperature.

In one or more embodiments, the amount of viscosity modifier is from about 0.01 to about 5 wt. %, in other embodiments, from about 0.05 to about 4 wt. %, and in other embodiments, from about 0.1 to about 3 wt. %, based upon the total weight of the mousse concentrate.

In one or more embodiments, the amount of viscosity modifier is from about 0.01 to about 5 wt. %, in other embodiments, from about 0.05 to about 4 wt. %, and in other embodiments, from about 0.1 to about 3 wt. %, based upon the total weight of the aerosol semi-permanent colorant composition, including propellant.

The mousse concentrate of the present invention may contain one or more cationic hair conditioning agents. In one or more embodiments, the cationic hair conditioning agent may facilitate the color penetration into the hair shaft. Examples include quaternary ammonium salts. In one or more embodiments, the cationic hair conditioning agent includes quaternium-80. Cationic hair conditioning agents are further described in U.S. Pat. Nos. 5,415,857, 4,000,077, 4,786,422, 4,888,119, and 4,929,367, all of which are incorporated herein by reference. Commercially available cationic hair conditioning agents include blends of quaternium-adide and propylene glycol, which are available from Univar under the trademark Abil Quat 3272, and from Sensient under the trademark Covafix 123.

In one or more embodiments, the amount of cationic hair conditioning agent is from about 0.01 to about 25 wt. %, in other embodiments, from about 0.05 to about 15 wt. %, and in other embodiments, from about 0.1 to about 10 wt. %, based upon the total weight of the mousse concentrate.

In one or more embodiments, the amount of cationic hair conditioning agent is from about 0.01 to about 25 wt. %, in other embodiments, from about 0.05 to about 15 wt. %, and in other embodiments, from about 0.1 to about 10 wt. %, based upon the total weight of the aerosol semi-permanent colorant composition, including propellant.

The mousse concentrate of the present invention may contain one or more preservatives. Examples of preservatives include 2-Bromo-2-Nitropropane-1,3-Diol, 4-Hydroxybenzoic Acid, 5-Bromo-5-Nitro-1,3-Dioxane, *Abies* Pectinate Wood Oil, *Achyranthes Japonica* Root/*Rhus semialata* Gall/*Terminalia Chebula* Fruit/*Glycyrrhiza Uralensis* Root/Stem Extract, Acrolein/Acrylic Acid Copolymer, *Alpinia speciosa* Flower/Leaf/Seed/Stem Extract, *Alpinia speciosa* Leaf/Stem, Ferment, *Alpinia uraiensis* Stalk/Leaf Water, Ammonium Benzoate, Ammonium Propionate, Ammonium Silver Zeolite, Ammonium Silver Zinc Aluminum Silicate, Anhydroxylityl Lactate, Bakuhan, Bamboo Vinegar, Benzethonium Chloride, Benzisothiazolinone, Benzoic Acid, Benzotriazole, Benzyl Alcohol, Benzylhemiformal, Benzylparaben, Bis-Aminoethoxyethane/Guanidine HCl Copolymer, *Boesenbergia pandurata* Rhizome Extract, Butyl Benzoate, Butylparaben, Calcium Benzoate, Calcium Paraben, Calcium Propionate, Calcium Salicylate, Calcium Sorbate, Capramidoethyl Capramidopropyldimonium Methosulfate, Caprylyl Glycol, Caprylyloxyphenylamino Dimethyltetrahydro Benzothiazine Carboxylic Acid, Captan, *Cassytha filiformis* Powder, Cetrimonium Bromide, Chloramine T, Chlorhexidine, Chlorhexidine Diacetate, Chlorhexidine Digluconate, Chlorhexidine Dihydrochloride, Chlorhexidine Diundecylenate, Chloroacetamide, Chlorobutanol, Chlorophene, Chlorothymol, Chloroxylenol, Citronellic Acid, *Citrus grandis* (Grapefruit) Fruit Extract, *Citrus grandis* (Grapefruit) Seed Extract, *Citrus grandis* Peel/Seed Extract, Copper Usnate, *Coriandrum sativum* (Coriander) Leaf Extract, DEDM Hydantoin, DEDM Hydantoin Dilaurate, Dehydroacetic Acid, Diazolidinyl Urea, Dibromocyanoacetamide, Dibromopropamidine Diisethionate, *Dictyophora indusiata* (Mushroom) Extract, *Dictyophora indusiata* Fruiting Body Extract, Dimethyl Hydroxymethyl Pyrazole, Dimethyl Oxazolidine, Dimethylaminostyryl Heptyl Methyl Thiazolium Iodide, Dimethylol Ethylene Thiourea, Dimethylol Glycol, Dimethylol Urea, Dithiomethylbenzamide, DMDM Hydantoin, DMHF, Domiphen Bromide, Egg Shell Membrane Extract, *Enterococcus faecalis* Ferment, Ethyl Benzoate, Ethyl Ferulate, Ethyl Lauroyl Arginate HCl, Ethylparaben, Ferulic Acid, Formaldehyde, Formic Acid, Galla Rhois Gallnut Extract, Glutaral, Glycerol Formal, Glyoxal, Hexamidine, Hexamidine Diisethionate, Hexamidine Diparaben, Hexamidine Paraben, Hexanediol/PEG-2 Cocomonium Chloride/TDI Copolymer, Hydroxyethoxyphenyl Butanone, Hydroxymethyl Dioxoazabicyclooctane, Imidazolidinyl Urea, Iodopropynyl Butylcarbamate, Isobutyl Benzoate, Isobutylparaben, Isodecylparaben, Isopropyl Benzoate, Isopropyl Cresols, Isopropyl Sorbate, Isopropylparaben, *Larix Sibirica* Wood Extract, Lauryl Diethylenediaminoglycine HCl, Lippia Origanoides Leaf/Flower/Stem Oil, m-Cresol, Macelignan, Magnesium Benzoate, Magnesium Propionate, Magnesium Salicylate, MDM Hydantoin, MEA o-Phenylphenate, MEA-Benzoate, MEA-Salicylate, MEK Peroxides, Methenamine, Methyl Benzoate, Methylchloroisothiazolinone, Methyldibromo Glutaronitrile, Methylisothiazolinone, Methylparaben, Mixed Cresols, Molybdic Acid, *Monarda fistulosa* Extract, *Murraya koenigii* Leaf Oil, Natamycin, Nisin, o-Cresol, o-Phenylphenol, Octylisothiazolinone, Oligopeptide-10, Oligopeptide-7, Oligopeptide-76, Oligopeptide-8, Oligopeptide-9, Ovotransferrin, p-Chloro-m-Cresol, p-Chlorophenol, p-Cresol, Panduratin A, Panthenyl Ethyl Ether Benzoate, Papenfussiella Kuromo Extract, PEG-15 DEDM Hydantoin, PEG-15 DEDM Hydantoin Stearate, PEG-5 DEDM, ydantoin, PEG-5 DEDM Hydantoin Oleate, Pentylene Glycol, Perillic Acid, Phenethyl Alcohol, Phenethyl Phenoxy, Methyldihydropyrroloquinoline HCl, Phenol, Phenoxyethanol, Phenoxyethylparaben, Phenoxyisopropanol, Phenyl Benzoate, Phenyl Mercuric Acetate, Phenyl Mercuric Benzoate, Phenyl Mercuric Borate, Phenyl Mercuric Bromide, Phenyl Mercuric Chloride, Phenylparaben, Piperlonguminine, Polyaminopropyl Biguanide, Polymethoxy Bicyclic Oxazolidine, Polyoxymethylene Glycol Urea, Polyquaternium-42, Potassium Benzoate, Potassium Butylparaben, Potassium Ethylparaben, Potassium Methylparaben, Potassium o-Phenylphenate, Potassium Paraben, Potassium Phenoxide, Potassium Propionate, Potassium Propylparaben, Potassium Salicylate, Potassium Sorbate, Propionic Acid, Propyl Benzoate, Propylparaben, *Pseudomonas aeroginosa* Culture Conditioned Media Extract, Punica Granatum Peel Extract, Quaternium-14, Quaternium-15, Quaternium-8, Silver Borosilicate, Silver Citrate, Silver Magnesium Aluminum Phosphate, Sodium Benzoate, Sodium Butylparaben, Sodium Calcium Copper Phosphate, Sodium Citronellate, Sodium Dehydroacetate, Sodium Ethylparaben, Sodium Formate, Sodium Hydroxymethane Sulfonate, Sodium Hydroxymethylglycinate, Sodium Isobutylparaben, Sodium Isopropylparaben, Sodium Lauryl Diethylenediaminoglycinate, Sodium Mannitylphytate, Sodium Methylparaben, Sodium o-Phenylphenate, Sodium p-Chloro-m-Cresol, Sodium Paraben, Sodium Phenolsulfonate, Sodium Phenoxide, Sodium Phosphorus/Zinc/Calcium/Silicon/Aluminum/Silver Oxides, Sodium Propionate, Sodium Propylparaben, Sodium Pyrithione, Sodium Salicylate, Sodium Sorbate, Sorbic Acid, *Spiraea thunbergii* Leaf Extract, TEA-Sorbate, Terephthalaldehyde, Tetramethylolglycoluril, Thiamine Bis-Laurylsulfate, Thianthol, Thimerosal, *Thymus Vulgaris* (Thyme) Leaf Oil, Titanium Salicylate, Triclocarban, Triclosan, Tris (N-Hydroxyethyl) Hexahydrotriazine, Tris(N-Hydroxypropyl) Hexahydrotriazine, Undecylenoyl PEG-5 Paraben, Zinc Pyrithione, Zinc Salicylate.

In one or more embodiments, examples include phenoxyethanol, methylparaben, ethylparaben, and propylparaben. In one or more embodiments, the preservative includes phenoxyethanol.

In one or more embodiments, the amount of preservative is from about 0.01 to about 5 wt. %, in other embodiments, from about 0.05 to about 4 wt. %, and in other embodiments, from about 0.1 to about 3 wt. %, based upon the total weight of the mousse concentrate.

In one or more embodiments, the amount of preservative is from about 0.01 to about 5 wt. %, in other embodiments, from about 0.05 to about 4 wt. %, and in other embodiments, from about 0.1 to about 3 wt. %, based upon the total weight of the aerosol semi-permanent colorant composition, including propellant.

In some embodiments, a semi-permanent colorant composition comprises an aqueous carrier. In one or more embodiments, the mousse concentrate includes from about 40 to about 98 wt. % water, in other embodiments, from about 45% to about 95 wt. %, in other embodiments, from about 50 to about 90 wt. %, based upon the total weight of the mousse concentrate.

In embodiments where a semi-permanent colorant composition is provided as an aerosol, the total wt. % of the water may be from about 40 wt. % to about 95 wt. %, in other embodiments, from about 45% to about 90%, in other embodiments, from about 50% to about 85 wt. %, based upon the total weight of the semi-permanent colorant composition.

Advantageously, the amount of organic carrier may be limited. Organic carriers include volatile liquids. In some cases, organic carriers include volatile alcohols such as ethanol and isopropanol. In some cases, organic carriers include volatile silicone compounds. Volatile silicone compounds generally have an atmospheric pressure boiling point of less than about 220° C., or between about 50° C. and about 220° C., and contain between about 3 and about 7 silicon atoms. Non-limiting examples of volatile silicone compounds include polydimethylsiloxanes (e.g., having a viscosity less than about 5 cSt at 25° C.), cyclomethicone, cyclohexane siloxane, decamethyltetrasiloxane, octamethyltrisiloxane, decamethylpentasiloxane, decamethylcyclopentasiloxane, octamethylcyclotetrasiloxane, trimethylsilylamodimethicone, phenyl trimethicone, hexamethyidisiloxane, dimethylsiloxane/methylalkylsiloxane, or combinations thereof.

In one or more embodiments the mousse concentrate includes less than about 20 wt. % of the non-aqueous organic carrier material, in other embodiments, less than about 15 wt. %, in other embodiments, less than about 10 wt. %, in other embodiments, less than about 5 wt. %, in other embodiments, less than about 1 wt. %, based upon the total weight of the mousse concentrate.

In embodiments where a semi-permanent colorant composition is provided as an aerosol, the total percentage weight of the non-aqueous organic carrier material may be less than about 20 wt. %, in other embodiments, less than about 15 wt. %, in other embodiments, less than about 10 wt. %, in other embodiments, less than about 5 wt. %, in other embodiments, less than about 1 wt. %, based upon the total weight of the semi-permanent colorant composition.

In some embodiments, the semi-permanent colorant composition may comprise at one or more additional optional ingredients. Non-limiting examples of additional optional components include antioxidants, essential oils, perfumes, waxes, fillers, hair-fixative polymers, deodorizing agents, pediculicides, anti-dandruff agents, cosmetic and/or dermatological active agents including emollients, moisturizers, vitamins (e.g., vitamin B complexes (e.g., including thiamine, nicotinic acid, biotin, pantothenic acid, choline, riboflavin, vitamin B6, vitamin B12, pyridoxine, inositol, carnitine), vitamins A, C, D, E, K and their derivatives (e.g., vitamin A palmitate) or pro-vitamins), essential fatty acids, sunscreens, herb and/or plant extracts (e.g., aloe), dispersing or suspending agents (e.g., silica); pharmaceutically active agents (e.g., poly(2-hydroxystearic acid); anti-static agents (e.g., tricetyl methyl ammonium chloride); pearlescent aids (e.g., such as coated mica, ethylene glycol distearate), opacifiers (e.g., tin), odor neutralizers, sequestering agents, and combinations thereof.

In one or more embodiments, the semi-permanent colorant composition may include a deodorizing agent. Non-limiting examples of deodorizing agents include cyclodextrins, zinc undecylenate, undecylenic acid, natural fragrance oils, and combinations thereof.

The identity and amount of each optional ingredient is not particularly limited, so long as they do not deleteriously affect the performance of the semi-permanent hair colorant composition. Generally, one of ordinary skill in the art can determine the effective amount of each optional ingredient. Typically, the effective amount of an optional ingredient will be from about 0.01% to about 10 wt. %, in other embodiments, from about 0.01% to about 5 wt. %, in other embodiments, from about 0.1% to about 3 wt. %, in other embodiments, from about 0.01% to about 1 wt. %, in other embodiments, from about 0.1% to about 5 wt. %, in other embodiments, from about 1% to about 5 wt. %, based upon the total weight of the mousse concentrate.

Typically, the effective amount of an optional ingredient will be from about 0.01 to about 10 wt. %, in other embodiments, from about 0.01 to about 5 wt. %, in other embodiments, from about 0.1 to about 3 wt. %, in other embodiments, from about 0.01% to about 1 wt. %, in other embodiments, from about 0.1% to about 5%, in other embodiments, from about 1% to about 5 wt. %, based upon the total weight of the semi-permanent colorant composition.

The mousse concentrate may be prepared by any suitable method. In one or more embodiments, the non-colorant solids may be dissolved or dispersed in water with mixing, and then other ingredients are added. In one or more embodiments, the colorant is added last.

The semi-permanent colorant composition may be prepared using any suitable technique, as will be known to those of ordinary skill in the art. In some cases, the semi-permanent colorant composition may be prepared by mixing an appropriate amount of a liquefied gaseous propellant and a mousse concentrate under pressure, followed by packing the mixture in an aerosol container. In other cases, an aerosol container may be loaded with a mousse (e.g., as a powder, slurry, or liquid), followed by pressurizing the container with a propellant and sealing the container.

The aerosol container is not particularly limited, and may be any container or dispenser suitable for mousse delivery. The aerosol container may be formed of any suitable material, for example, metal (e.g., aluminum), glass, plastic, or combinations thereof. In most embodiments, the aerosol container is formed essentially of metal. The container may comprise a dip tube and/or a spray nozzle.

A semi-permanent colorant composition is provided that exhibits excellent color deposit without heat or oxidative treatment, and resists fading throughout several washes. Thus, the present invention further provides a method for the semi-permanent coloring of hair.

The method includes the steps of providing an aerosolized mousse semi-permanent colorant composition according to the present invention, massaging an amount of the colorant composition onto hair, allowing the composition to remain on the hair for an effective period of time, and rinsing the excess composition from the hair. Advantageously, heat is not required.

The semi-permanent colorant composition may be applied to target areas using an aerosol dispenser. The semi-permanent colorant composition may be applied to wet or dry hair.

The semi-permanent colorant composition may be left on the hair for an effective time. An effective time is the amount of time that is sufficient to cause color to develop. In one or more embodiments, the effective time is from about 3 to about 45 minutes, in other embodiments, from about 5 to about 15 minutes. In one or more embodiments, the effective time is up to about 45 minutes, in other embodiments, up to about 40 minutes, in other embodiments, up to about 35 minutes, in other embodiments, up to about 30 minutes, in other embodiments, up to about 25 minutes, in other embodiments, up to about 20 minutes, in other embodiments, up to about 10 minutes. In one or more embodiments, the effective time is at least about 3 minutes, in other embodiments, at least about 5 minutes, in other embodiments, at least about 10 minutes.

After the effective period of time has elapsed, the user may simply rinse the excess semi-permanent colorant composition out of the hair using water. The user may wash and/or dry the hair as desired.

In one or more embodiments, the method of application of the semi-permanent colorant composition may include a pre-step of lightening the target hair. Methods of lightening hair are known in the art.

The aerosol mousse semi-permanent colorant compositions provide ease of application. The compositions are ammonia free. The colors are very bright, and maintain an excellent level of color-fastness even after multiple shampoos. In one or more embodiments, color remains on the hair after six shampoos, in other embodiments, after eight shampoos, in other embodiments, after ten shampoos. In one or more embodiments, color is maintained through at least twelve shampoos, in other embodiments, through at least fourteen shampoos.

EXAMPLES

Semi-permanent colorant mousse concentrates with a stearate-based viscosity adjuster and a non-stearate-based viscosity adjuster:

A composition was prepared according to the ingredients and amounts shown in Table 1. After several days, it was observed that the composition had separated. A similar composition was prepared, but with a starch-based viscosity modifier. After several days, no separation was observed.

Various modifications and alterations that do not depart from the scope and spirit of this invention will become apparent to those skilled in the art. This invention is not to be duly limited to the illustrative embodiments set forth herein.

What is claimed is:

1. A semi-permanent hair colorant mousse concentrate comprising:
   at least one colorant;
   at least one foam-boosting surfactant;
   at least one cold process agent;
   a viscosity modifier selected from starch and modified starch, wherein the modified starch is hydroxypropyl starch phosphate; and
   at least 2 wt. % aqueous carrier, based upon the total weight of the composition.

2. The mousse concentrate of claim 1, where the at least one colorant is selected from the group consisting of direct dyes, disperse dyes, acid dyes, and basic dyes.

3. The mousse concentrate of claim 1, where the at least one foam-boosting surfactant is a surfactant selected from the group consisting of nonionic surfactants, zwitterionic surfactants, anionic surfactants, and combinations thereof.

4. The mousse concentrate of claim 1, wherein the at least one foam-boosting surfactant is a nonionic surfactant selected from the group consisting of polyethylene condensates of alkyl phenols, polypropylene condensates of alkyl phenols, polybutylene oxide condensates of alkyl phenols, fatty acid amide surfactants, polyhydroxy fatty acid amide surfactants, amine oxide surfactants, alkyl ethoxylate sur-

TABLE 1

|  | Trade Name | INCI Name | % W/W |
| --- | --- | --- | --- |
| Water | Water | Water | 88.970 |
| Colorant | 306085 Arianor Jade Blue | HC Blue 15 | 0.02 |
| Cold process agent | Jeesperse ICE-T CPCS | Cetearyl Alcohol | 2.000 |
|  |  | Behentrimonium Chloride |  |
|  |  | Polyquaternium-37 |  |
| Foam Boosting Surfactant | JEETERIC CAB-LC | Cocamidopropyl Betaine | 3.000 |
| Conditioning Agent | CovaFIX 123 | Propylene Glycol | 3.000 |
|  |  | Benzyl Alcohol |  |
|  |  | Quaternium-80 |  |
| Viscosity agent | Versathix | PEG-150 Pentaerythrityl Tetrastearate | 1.000 |
|  |  | PPG-2 Hydroxyethyl Cocamide |  |
|  |  | Water |  |
| Optional ingredient | SalSphere Color Guard | Water (and) Euphorbia Cerifera (Candelilla) | 2.000 |
|  |  | Wax (and) Polysorbate 80 (and) |  |
|  |  | Butyrospermum Parkii (Shea) Butter (and) |  |
|  |  | Brassica Oleracea Italica (Broccoli) Seed Oil |  |
|  |  | (and) Ethylhexyl Methoxycinnamate (and) |  |
|  |  | Polyquaternium-67 (and) Sorbitan Oleate (and) |  |
|  |  | Hydroxypropyl Guar Hydroxypropyltrimonium |  |
|  |  | Chloride (and) Octyldodecanol (and) Beeswax |  |
|  |  | (and) Vaccinium Macrocarpon (Cranberry) Seed |  |
|  |  | Oil (and) Phenethyl Alcohol (and) Caprylyl |  |
|  |  | Glycol (and) Ethylhexylglycerin |  |
| Preservative | AMP-95 | Aminomethyl Propanol | 0.010 |
|  |  |  | 100.000 | factants, alkanoyl glucose amide surfactants, alkylpolyglycosides and combinations thereof.

5. The mousse concentrate of claim 1, wherein the at least one foam-boosting surfactant is a nonionic surfactant selected from the group consisting of cocamide DEA, cocamide MEA, cocamide MIPA, lauramide DEA, lauramide MEA, lauramine oxide, cocamine oxide, cocamidopropylamine oxide, lauramidopropylamine oxide, sorbitan laurate, sorbitan distearate, lauryl alcohol, laureth-4, laureth-7, laureth-9, laureth-40, trideceth alcohol, C11-15 pareth-9, C12-13 Pareth-3, and C14-15 Pareth-11, decyl glucoside, lauryl glucoside, coco glucoside, and combinations thereof.

6. The mousse concentrate of claim 1, wherein the at least one foam boosting surfactant is a zwitterionic surfactant selected from the group consisting of cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, cocodimethyl sulfopropyl betaine, stearyldimethyl sulfopropyl betaine, lauryl dimethyl sulfoethyl betaine, lauryl bis-(2-hydroxy-ethyl)sulfopropyl betaine, alkylamidopropylhydroxy sultaines and combinations thereof.

7. The mousse concentrate of claim 1, wherein the at least one foam boosting surfactant is an anionic surfactant selected from the group consisting of monoalkyl phosphates, dialkyl phosphates, sarcosinates, sulfosuccinates, isethionates, taurates, sodium cocoyl glycinate, sodium lauryl glycinate, sodium cocoyl alinate, glutamates, and mixtures thereof.

8. The mousse concentrate of claim 1, wherein the at least one foam boosting surfactant is an anionic surfactant selected from the group consisting of lauramidopropyl hydroxysultaine, sodium lauroamphoacetate, sodium cocoyl glycinate, sodium methyl cocoyl taurate, and decyl glucoside, sodium-monoalkyl phosphates, sodium dialkyl phosphates, sodium lauroyl sarcosinate, lauroyl sarcosine, cocoyl sarcosinate, sodium cocoyl isethionate, disodium laureth sulfosuccinate, sodium methyl oleoyl taurate, sodium methyl cocoyl taurate, sodium laureth carboxylate, sodium trideceth carboxylate, and combinations thereof.

9. The mousse concentrate of claim 1, wherein the cold process agent comprises cetearyl alcohol, behentrimonium chloride, and polyquaternium-37.

10. The mousse concentrate of claim 1, wherein the mousse concentrate further comprises a cationic conditioning agent selected from the group consisting of quaternary ammonium salts.

11. The mousse concentrate of claim 1, wherein the mousse concentrate further comprises one or more preservatives.

12. A water-based aerosol mousse semi-permanent colorant composition comprising:
a mousse concentrate comprising:
at least one colorant;
at least one foam-boosting surfactant;
at least one cold process agent;
a viscosity modifier selected from starch and modified starch, wherein the modified starch is hydroxypropyl starch phosphate; and
at least 2 wt. % aqueous carrier, based upon the total weight of the composition; and
a propellant.

13. The aerosol mousse semi-permanent colorant composition of claim 12, wherein the propellant is selected from the group consisting of hydrocarbons, hydrofluorocarbons, ethers, and combinations thereof.

14. The aerosol mousse semi-permanent colorant composition of claim 12, wherein the propellant is selected from the group consisting of pentane, n-butane, isobutane, propane, 1,1,1,2-tetrafluoroethane (134a), 1,1-difluoroethane (152a), dimethyl ether, and combinations thereof.

15. The aerosol mousse semi-permanent colorant composition of claim 12, wherein the propellant comprises butane and propane.

16. The aerosol mousse semi-permanent colorant composition of claim 12, wherein the composition does not include any stearate compounds.

17. The aerosol mousse semi-permanent colorant composition of claim 12, wherein the total amount of propellant is from about 4 to about 15 wt. %, based upon the total weight of the composition.

* * * * *